(12) United States Patent  (10) Patent No.: US 7,049,275 B2
Ikemoto et al.  (45) Date of Patent: May 23, 2006

(54) PHOTORESIST STRIPPING COMPOSITION AND CLEANING COMPOSITION

(75) Inventors: Kazuto Ikemoto, Tokyo (JP); Yoshiaki Yamamoto, Niigata (JP); Hiroshi Yoshida, Chiba (JP); Taketo Maruyama, Chiba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 339 days.

(21) Appl. No.: 10/385,721

(22) Filed: Mar. 12, 2003

(65) Prior Publication Data

US 2003/0181344 A1   Sep. 25, 2003

(30) Foreign Application Priority Data

Mar. 12, 2002 (JP) ............................... 2002-66529
Jun. 24, 2002 (JP) ............................. 2002-183711

(51) Int. Cl.
  *C11D 7/50* (2006.01)
(52) U.S. Cl. ...................... 510/176; 510/175; 510/255; 510/245; 510/499; 134/1.3; 134/2
(58) Field of Classification Search ................ 510/176, 510/175, 499, 212, 202; 134/2, 3, 38, 40
  See application file for complete search history.

(56) References Cited

U.S. PATENT DOCUMENTS 5,567,574 A * 10/1996 Hasemi et al. .............. 475/316
5,989,353 A * 11/1999 Skee et al. ...................... 134/2
6,413,647 B1 * 7/2002 Hayashi et al. ............. 428/447

* cited by examiner

*Primary Examiner*—Gregory E. Webb
(74) *Attorney, Agent, or Firm*—Antonelli, Terry, Stout and Kraus, LLP.

(57) ABSTRACT

The photoresist stripping composition of the present invention contains at least one oxymethylamine compound represented by the following formula 1:

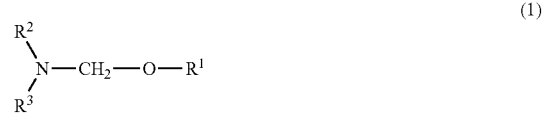

wherein $R^1$ to $R^3$ are as defined in the specification. Of the oxymethylamine compound of the formula 1, the compound represented by the following formula 7:

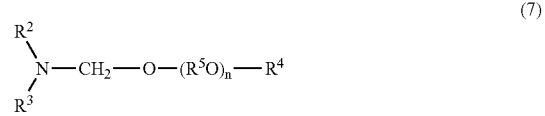

wherein $R^2$ to $R^5$ and n are as defined in the specification, is a novel compound.

35 Claims, 2 Drawing Sheets

PHOTORESIST STRIPPING COMPOSITION AND CLEANING COMPOSITION

BACKGROUND OF THE INVENTION

1. Field of the Invention

Photoresists have been used in the lithographic production of wide range of devices including integrated circuits such as LC and LSI, display devices such as LCD and EL device, printed boards, micro machines, DNA chips and micro plants. The present invention relates, particularly, to a photoresist stripping composition for removing photoresists from various substrates carrying the photoresists.

Amine compounds, with their alkaline and nucleophilic natures, have been used for cleaning integrated circuits, liquid crystal display devices and printed boards and for removing photoresists applied on the substrates of these devices. The present invention further relates to a novel amine compound optimum for use in these purposes, a production method thereof, a cleaning composition and a photoresist stripping composition containing the novel amine compound.

2. Description of the Prior Art

Alkaline stripping compositions have been conventionally used for removing photoresists. For example, TOK106 available from Tokyo Oka Co., Ltd. comprises an alkanolamine and dimethyl sulfoxide, and EKC265 available from EKC Technology Co., Ltd. comprises an alkanolamine, hydroxylamine, catechol and water. U.S. Pat. No. 4,276,186 discloses a composition comprising N-methylpyrrolidone and ethanolamine, and Japanese Patent Application Laid-Open No. 4-289866 discloses a composition comprising an alkanolamine and hydroxylamine.

These alkanolamines have been synthesized by the reaction of a corresponding alkylene oxide and ammonia as described in "Industrial Organic Chemistry", 4th ed., p175, Tokyo Kagaku Dojin Co., Ltd. edited by Sakiyama Mitsuaki. These alkanolamines are very inexpensive because produced by a simple process. However, the use of the alkanolamine alone cannot meet the recent requirement in the production of semiconductor devices and liquid crystal display panels, particularly, with respect to the fine processing and short-term processing. To meet the requirement, Japanese Patent Application Laid-Open Nos. 11-194505 and 6-266119 disclose compositions containing hydroxylamine. The composition containing hydroxylamine shows a high resist removal. However, hydroxylamine is disadvantageous because easily decomposed, this making the purification thereof difficult to significantly increase its cost.

As a compound free from these drawbacks and capable of effectively enhancing the resist removal, Japanese Patent Application Laid-Open No. 2000-250230 discloses hydroxymethylamine. Although, hydroxymethylamine is stable as compared with hydroxylamine, the hydroxyl group contained therein increases the viscosity. Recently, semiconductor devices for semiconductor integrated circuits and liquid crystal display devices have come to be produced from various materials, requiring a photoresist stripping composition free from corrosion of various substrate materials.

SUMMARY OF THE INVENTION

An object of the present invention is to solve the prior art problems on the resist stripping and to provide a photoresist stripping composition that is capable of easily removing, at low temperatures in a short period of time, photoresist layers applied on substrates, photoresist layers remaining after etching, photoresist residues after ashing subsequent to etching. Another object of the present invention is to provide a photoresist stripping composition that is capable of removing photoresist layers and photoresist residues without corroding the materials of substrates being treated, thereby enabling the fine processing and producing high precision circuits. Still another object of the present invention is to provide a method for removing photoresists using the photoresist stripping composition. Still another object of the present invention is to provide a novel amine compound suitable as a component for the photoresist stripping composition.

As a result of extensive study, the inventors have found that a composition containing an alkoxymethylamine compound removes photoresist layers and photoresist residues remaining on substrates after etching and photoresist residues remaining after ashing subsequent to etching easily at low temperatures in a short period of time. The inventors further found that such a composition removes photoresists without corroding wiring materials and insulating layers to enable the fine processing and provide high precision circuits. The inventors have still further found that a novel alkoxymethylamine compound that is substituted by an ether linkage-containing substituent (hereinafter referred to as "novel oxymethylamine compound") is effective for photoresist removal.

DETAILED DESCRIPTION OF THE INVENTION

Figure 1:
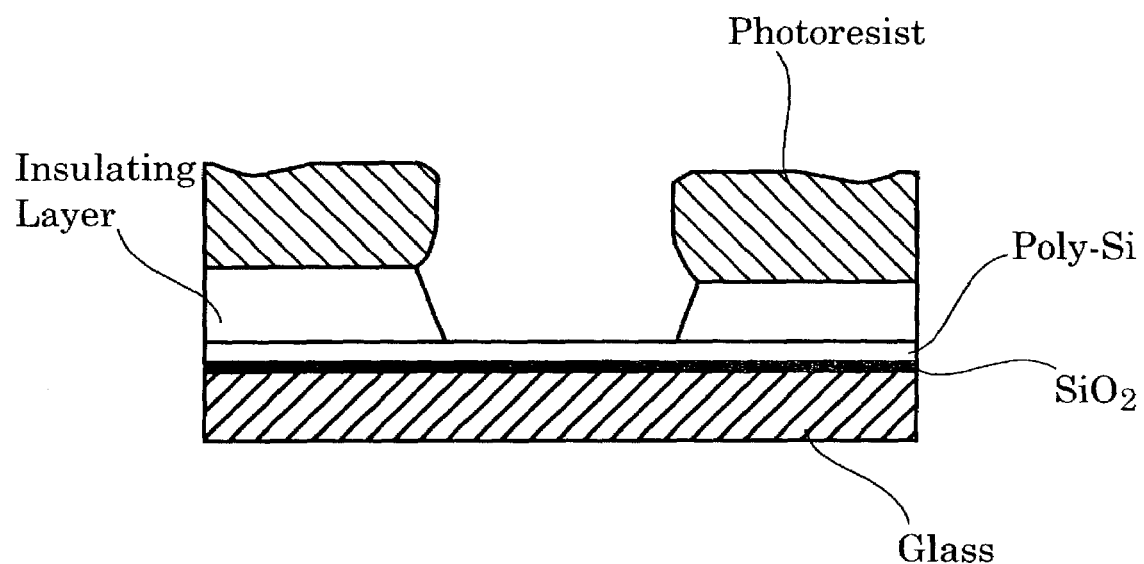
FIG. 1 is a cross-sectional schematic view of the test substrates used in Examples 18–21 and 25–29 and Comparative Examples 5–6 and 8–10, showing a partially exposed polysilicon layer.

The photoresist stripping composition of the present invention contains at least one oxymethylamine compound (alkoxymethylamine compound+novel oxymethylamine compound), which is specifically represented by the following formula 1:

wherein $R^1$ is alkyl group, hydroxyalkyl group, aryl group, acyl group, alkoxyalkyl group, aminoalkyl group, or ether linkage-containing substituent; $R^2$ is hydrogen, alkyl group, acyl group, hydroxyalkyl group, aryl group, allyl group, aminoalkyl group, alkoxyalkyl group, hydroxyl group, or amino group; $R^3$ is hydrogen, alkyl group, acyl group, hydroxyalkyl group, aryl group, allyl group, aminoalkyl group, alkoxyalkyl group, hydroxyl group, or amino group. $R^2$ and $R^3$ together with the nitrogen to which $R^2$ and $R^3$ are bonded may form a ring structure such as morpholine ring, piperidine ring and piperazine ring when each of $R^2$ and $R^3$ is a group having 1 to 8 carbon atoms. The oxymethylamine compounds of the formula 1 wherein $R^1$ is the ether linkage-containing substituent are novel. In the definition of $R^1$ to $R^3$, the term "alkyl", used either alone or in compound words such as "hydroxyalkyl", "alkoxyalkyl" and "aminoalkyl" includes straight-chain alkyl having 1 to 14 carbon atoms or branched alkyl having 3 to 14 carbon atoms. Acyl group preferably has 2 to 6 carbon atoms. Examples of aryl groups are phenyl group and naphthyl group.

The oxymethylamine compound includes the basic structure of hydroxymethylamine disclosed in Japanese Patent Application Laid-Open No. 2000-250230, represented by the following formula 6:

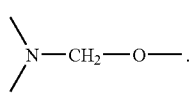
(6)

The present invention is based on the finding that the oxymethylamine compound having the formula 1 is effective for removing the detrimental affect of the hydroxyl group of hydroxymethylamine.

The oxymethylamine compounds of the formula 1 wherein $R^1$ is alkyl group, hydroxyalkyl group, alkoxyalkyl group or ether linkage-containing substituent are preferable because of their easy availability and easy production. The boiling point of the oxymethylamine compound is preferably 40° C. or higher. If less than 40° C., the oxymethylamine compound may escape to change the chemical composition of photoresist stripping composition.

The oxymethylamine compound used in the present invention has in one molecule at least one oxymethylamine structure (>N—CH$_2$—O—R$^1$), while two or more oxymethylamine structures in one molecule create no adverse affect. The oxymethylamine compound may be in a salt form with inorganic acid or organic acid.

Examples of the alkoxymethylamine compounds (oxymethylamine compounds of the formula 1 wherein $R^1$ is group other than the ether linkage-containing substituent) include (butoxymethyl)diethylamine, (methoxymethyl)diethylamine, (methoxymethyl)dimethylamine, (butoxymethyl)dimethylamine, (isobutoxymethyl)dimethylamine, N-(methoxymethyl)morpholine, N-(butoxymethyl)morpholine, N-(methoxymethyl)piperidine, N-(butoxymethyl)piperidine, di(methoxymethyl)aminoethane, di(methoxymethyl)aminomethane, di(butoxymethyl)aminoethane, di(butoxymethyl)aminomethane, di(methoxymethyl)aminoethanol, di(butoxymethyl)aminoethanol, di(methoxymethyl)aminoethoxyethanol, di(butoxymethyl)aminoethoxyethanol, di(methoxymethyl)aminoethoxymethane, methyl(methoxymethyl)aminoethane, methyl(methoxymethyl) aminoethanol, methyl(butoxymethyl)aminoethanol, di(methoxymethyl)aminopropanol, di(butoxymethyl)aminopropanol, di(methoxymethyl)aminoisopropanol, di(butoxymethyl)aminoisopropanol, N,N-di(methoxymethyl)-N', N'-dimethylethylenediamine, N,N'-di(methoxymethyl) piperazine, di(butoxymethyl)piperazine, (methoxymethyl) diethanolamine, and (hydorxyethyloxymethyl) diethylamine. The alkoxymethylamine compound is not limited to those cited above, and may include a compound having in one molecule at least one oxymethylamine structure.

As a production method of amine compounds having the structure of formula 6, G. M. Robinson, R. Robinson, J. Chem. Soc., 123, 523 (1923) reports the production of an alkoxymethylamine compound of formula 1 wherein $R^1$ is alkyl group. Although effective for enhancing the resist removal, such an amine compound is insufficient in water solubility and is smelling. As a result of study on molecular design for improving the water solubility and reducing the smelling, it has been found by the inventors that the novel oxymethylamine compound of formula 1 wherein $R^1$ is the ether linkage-containing substituent is effective for the improvement.

The novel oxymethylamine compound is preferably represented by the following formula 7:

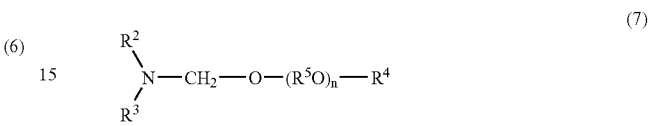
(7)

wherein $R^2$ and $R^3$ are as defined above; $R^4$ is a straight-chain or branched alkyl group having 1 to 8, preferably 1 to 4 carbon atoms; $R^5$ is a straight-chain or branched alkylene group having 1 to 4, preferably 2 or 3 carbon atoms; and n is an integer from 1 to 4, preferably 1 or 2. Two or more $R^5$ groups when n is an integer from 2 to 4 may be the same or different.

In view of further improving the water solubility, the following ether linkage-containing substituent having more ether linkages, represented by the following formula 2:

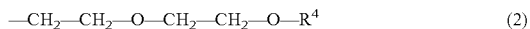
(2)

wherein $R^4$ is as defined above, is preferred.

More preferred is the following ether linkage-containing substituent derived from propylene glycol of higher safety, represented by the following formula 3:

(3)

wherein $R^4$ is defined above.

Particularly preferred compounds of formula 1 wherein $R^1$ is the ether linkage-containing substituent are the novel oxymethylamine compound represented by the following formula 4:

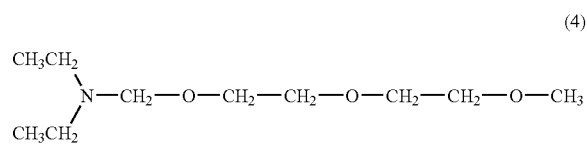
(4)

and the novel oxymethylamine compound represented by the following formula 5:

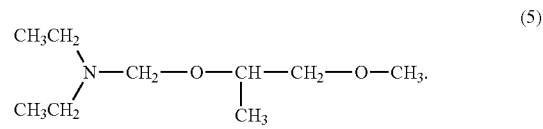
(5)

The novel oxymethylamine compound of formula 1 wherein $R^1$ is the ether linkage-containing substituent can be synthesized from an amine compound, formaldehyde and an ether linkage-containing alcohol according to the method described in G. M. Robinson, R. Robinson, J. Chem. Soc., 123, 523 (1923). In this method, the oxymethylamine compound is synthesized by dehydration reaction between the alcoholic hydroxyl group of hydroxymethylamine from the reaction of the amine compound and formaldehyde and the alcoholic hydroxyl group of the ether linkage-containing alcohol.

As the ether linkage-containing alcohol, glycol ethers are preferably used because of their easy availability. Examples thereof include ethylene glycol monoethyl ether, ethylene glycol monobutyl ether, diethylene glycol monomethyl ether, diethylene glycol monoethyl ether, diethylene glycol monobutyl ether, diethylene glycol, triethylene glycol, triethylene glycol monomethyl ether, triethylene glycol monoethyl ether, triethylene glycol monobutyl ether, propylene glycol monomethyl ether, propylene glycol monoethyl ether, propylene glycol monobutyl ether, dipropylene glycol monomethyl ether, dipropylene glycol monoethyl ether, and dipropylene glycol monobutyl ether.

The starting amine compound is not particularly limited, and primary amines and secondary amines may be used with no specific limitation. The amine compound is purified by a method generally used for organic compounds such as extraction, distillation and recrystallization.

Since the oxymethylamine compound acts as an amine compound, it is applicable to the cleaning of semiconductor devices in which amine compounds are conventionally used. The oxymethylamine compound of formula 1 wherein $R^1$ is the ether linkage-containing substituent is applicable to the cleaning in which ether compounds are conventionally used. The oxymethylamine compound having both ether linkage and amino group are particularly effective for cleaning semiconductors and also effective for fine processing of semiconductor devices because of its low corrosive properties.

The oxymethylamine compound is particularly effective for the resist removal. The reason therefor is not clear, but can be considered as follows. The aminomethyl radical after elimination of —O—$R^1$ from the oxymethylamine compound bonds to the phenolic hydroxyl group of photoresist, this increasing the solubility of photoresist to make the resist removal easy. In the presence of the alkaline composition mentioned below, the solubility of photoresist is further increased because of the promoted decomposition of photoresist, further enhancing the resist removal ability.

The photoresist stripping composition and cleaning composition of the present invention may contain an alkaline compound, an organic solvent, an anti-corrosion agent, and a surfactant, either alone or in combination.

Examples of the alkaline compounds include primary alkylamines such as methylamine, ethylamine, n-propylamine, isopropylamine, n-butylamine, sec-butylamine, isobutylamine, t-butylamine, pentylamine, 2-aminopentane, 3-aminopentane, 1-amino-2-methylbutane, 2-amino-2-methylbutane, 3-amino-2-methylbutane, 4-amino-2-methylbutane, hexylamine, 5-amino-2-methylpentane, heptylamine, octylamine, nonylamine, decylamine, undecylamine, dodecylamine, tridecylamine, tetradecylamine, pentadecylamine, hexadecylamine, heptadecylamine, and octadecylamine; secondary alkylamines such as dimethylamine, diethylamine, dipropylamine, diisopropylamine, dibutylamine, diisobutylamine, di-sec-butylamine, di-t-butylamine, dipentylamine, dihexylamine, diheptylamine, dioctylamine, dinonylamine, didecylamine, methylethylamine, methypropylamine, methylisopropylamine, methylbutylamine, methylisobutylamine, methyl-sec-butylamine, methyl-t-butylamine, methylamylamine, methylisoamylamine, ethylpropylamine, ethylisopropylamine, ethylbutylamine, ethylisobutylamine, ethyl-sec-butylamine, ethyl-t-butylamine, ethylisoamylamine, propylbutylamine, and propylisobutylamine; tertiary alkylamines such as trimethylamine, triethylamine, tripropylamine, tributylamine, tripentylamine, dimethylethylamine, methyldiethylamine, and methyldipropylamine; alkanolamines such as ethanolamine, N-methylethanolamine, N-ethylethanolamine, N-propylethanolamine, N-butylethanolamine, diethanolamine, isopropanolamine, N-methylisopropanolamine, N-ethylisopropanolamine, N-propylisopropanolamine, 2-aminopropane-1-ol, N-methyl-2-aminopropane-1-ol, N-ethyl-2-aminopropane-1-ol, 1-aminopropane-3-ol, N-methyl-1-aminopropane-3-ol, N-ethyl-1-aminopropane-3-ol, 1-aminobutane-2-ol, N-methyl-1-aminobutane-2-ol, N-ethyl-1-aminobutane-2-ol, 2-aminobutane-1-ol, N-methyl-2-aminobutane-1-ol, N-ethyl-2-aminobutane-1-ol, 3-aminobutane-1-ol, N-methyl-3-aminobutane-1-ol, N-ethyl-3-aminobutane-1-ol, 1-aminobutane-4-ol, N-methyl-1-aminobutane-4-ol, N-ethyl-1-aminobutane-4-ol, 1-amino-2-methylpropane-2-ol, 2-amino-2-methylpropane-1-ol, 1-aminopentane-4-ol, 2-amino-4-methylpentane-1-ol, 2-aminohexane-1-ol, 3-aminoheptane-4-ol, 1-aminooctane-2-ol, 5-aminooctane-4-ol, 1-aminopropane-2,3-diol, 2-aminopropane-1,3-diol, tris(oxymethyl)aminomethane, 1,2-diaminopropane-3-ol, 1,3-diaminopropane-2-ol, and 2-(2-aminoethoxy)ethanol; polyamines such as ethylenediamine, propylenediamine, trimethylenediamine, tetramethylenediamine, 1,3-diaminobutane, 2,3-diaminobutane, pentamethylenediamine, 2,4-diaminopentane, hexamethylenediamine, heptamethylenediamine, octamethylenediamine, nonamethylenediamine, N-methylethylenediamine, N,N-dimethylethylenediamine, trimethylethylenediamine, N-ethylethylenediamine, N,N-diethylethylenediamine, triethylethylenediamine, 1,2,3-triaminopropane, hydrazine, tris(2-aminoethyl)amine, tetra(aminomethyl)methane, diethylenetriamine, triethylenetetramine, tetraethylenepentamine, heptaethyleneoctamine, nonaethylenedecamine, and diazabicycloundecene; hydroxylamine compounds such as hydroxylamine, N-methylhydroxylamine, N-ethylhydroxylamine, N,N-diethylhydroxylamine, and O-methylhydroxylamine; cyclic amines such as pyrrole, 2-methylpyrrole, 3-methylpyrrole, 2-ethylpyrrole, 3-ethylpyrrole, 2,3-dimethylpyrrole, 2,4-dimethylpyrrole, 3,4-dimethylpyrrole, 2,3,4-trimethylpyrrole, 2,3,5-trimethylpyrrole, 2-pyrroline, 3-pyrroline, pyrrolidine, 2-methylpyrrolidine, 3-methylpyrrolidine, pyrazole, imidazole, 1,2,3-trizaole, 1,2,3,4-tetrazole, piperidine, 2-pipecoline, 3-pipecoline, 4-pipecoline, 2,4-lupetidine, 2,6-lupetidine, 3,5-lupetidine, piperazine, 2-methylpiperazine, 2,5-dimethylpiperazine, 2,6-dimethylpiperazine, and morpholine; and quaternary ammonium hydroxides such as tetraethylammonium hydroxide, tetrapropylammonium hydroxide, tetrabutylammonium hydroxide, chorine hydroxide, acetylchorine hydroxide. The oxymethylamine compound serves also as the alkaline compound. The alkaline compound usable in the present invention is not limited to those mentioned above, and any alkaline compound may be used without specific limitation. The alkaline compounds may be used alone or in combination of two or more.

Of the above alkaline compounds, preferred are methylamine, ethylamine, propylamine, butylamine, ethanolamine, N-methylethanolamine, N-ethylethanolamine, diethanolamine, isopropanolamine, 2-(2-aminoethoxy)ethanol, ethylenediamine, propylenediamine, butylenediamine, diethylenetriamine, piperazine, and morpholine.

The organic solvent is not particularly limited as far as miscible with the oxymethylamine compound. Water-soluble organic solvent are preferably used. Examples thereof include ether solvents such as ethylene glycol, ethylene glycol monoethyl ether, ethylene glycol monobutyl ether, diethylene glycol monomethyl ether, diethylene glycol monoethyl ether, diethylene glycol monobutyl ether, propylene glycol monomethyl ether, propylene glycol monoethyl ether, propylene glycol monobutyl ether, dipropylene glycol monomethyl ether, dipropylene glycol monoethyl ether, dipropylene glycol monobutyl ether, diethylene glycol dimethyl ether and dipropylene glycol dimethyl ether; amide solvents such as formamide, monomethylformamide, dimethylformamide, monoethylformamide, diethylformamide, acetamide, monomethylacetamide, dimethylacetamide, monoethylacetamide, diethylacetamide, N-metylpyrrolidone and N-ethylpyrrolidone; alcohol solvents such as methyl alcohol, ethyl alcohol, isopropanol, ethylene glycol and propylene glycol; sulfoxide solvents such as dimethyl sulfoxide; sulfone solvents such as dimethyl sulfone, diethyl sulfone, bis(2-hydroxy) sulfone and tetramethylene sulfone; imidazolidinone solvents such as 1,3-dimethyl-2-imidazolidinone, 1,3-diethyl-2-imidazolidinone and 1,3-diisopropyl-2-imidazolidinone; and lactone solvents such as γ-butyrolactone and δ-valerolactone.

Of the above solvents, preferred are dimethyl sulfoxide, N,N-dimethylformamide, N,N-dimethylacetamide, N-methylpyrrolidone, diethylene glycol monomethyl ether, diethylene glycol monobutyl ether, dipropylene glycol monomethyl ether, dipropylene glycol monobutyl ether, and propylene glycol, because of their easy availability and high boiling points.

The anti-corrosion agent may include aromatic hydroxy compounds, sugar alcohols, triazole compounds and chelating compounds.

Examples of the aromatic hydroxy compounds include phenol, cresol, xylenol, pyrocatechol, t-butylcatechol, resorcinol, hydroquinone, pyrogallol, 1,2,4-benzenetriol, salicyl alcohol, p-hydroxybenzyl alcohol, o-hydroxybenzyl alcohol, p-hydroxyphenethyl alcohol, p-aminophenol, m-aminophenol, diaminophenol, aminoresorcinol, p-hydroxybenzoic acid, o-hydroxybenzoic acid, 2,4-dihydroxybenzoic acid, 2,5-dihydroxybenzoic acid, 3,4-dihydroxybenzoic acid, 3,5-dihydroxybenzoic acid and gallic acid.

Examples of the sugar alcohols include sorbitol, xylitol and palatinit. Examples of the triazole compounds include benzotriazole, aminotriazole and aminotetrazole.

Examples of the chelating compounds include phosphoric acid compounds such as 1,2-propanediaminetetramethylene phosphonic acid and hydroxyethane phosphonic acid; caboxylic acids such as ethylenediaminetetraacetic acid, dihydroxyethylglycine, nitrilotriacetic acid, oxalic acid, citric acid, malic acid and tartaric acid; amines such as bipyridine, tetraphenylporphyrin, phenanthroline and 2,3-pyridinediol; oxime compounds such as dimethylglyoxime and diphenylglyoxime; and acetylene compounds such as phenylacetylene and 2,5-dimethyl-3-hexyne-2,5-diol.

These compounds may be used alone or in combination of two or more.

The surfactant may be cationic, anionic, nonionic, or amphoteric.

The concentration of the oxymethylamine compound in the photoresist stripping composition or the cleaning composition is 0.001 to 100% by weight, preferably 0.01 to 50% by weight. The oxymethylamine compound serves as an alkali, therefore, the oxymethylamine compound alone can be used in the photoresist removal and the cleaning.

The concentration of the alkaline compound, if used, is 0.001 to 99.999% by weight, preferably 0.1 to 90% by weight of the photoresist stripping composition or the cleaning composition.

The concentration of the organic solvent is not particularly limited, and can be determined according to the viscosity or specific gravity of the photoresist stripping composition or the cleaning composition, etching conditions, ashing conditions, etc. If used, the concentration is preferably 99% by weight or less of the photoresist stripping composition or the cleaning composition.

The addition amount of the anti-corrosion agent is not particularly limited, and preferably 30% by weight or less, more preferably 15% by weight or less of the photoresist stripping composition or the cleaning composition.

Water is optionally used. The concentration is, if used, determined by taking etching conditions and ashing conditions into consideration. Usually, the concentration is 50% by weight or less.

The method for removing photoresist of the present invention comprises a step of etching an electrically conductive layer on a substrate using a patterned photoresist layer as the mask to remove the non-masked region of the electrically conductive layer, and a step of removing the photoresist layer remaining after the etching by contact treatment with the photoresist stripping composition. After the etching, the ashing treatment may be carried out, if desired. Then, the etching residues are removed by the photoresist stripping composition. The ashing treatment referred to herein is a method of removing photoresists made of organic polymer by combustion to CO and $CO_2$ in oxygen plasma.

The contact between the remaining photoresist layer and the etching residues with the photoresist stripping composition is usually carried out at a temperature from ordinary temperature (about 20° C.) to 150° C. for 0.1 to 60 min. To prevent the attack to the substrate materials, the contact temperature is preferably as low as possible. Using the photoresist stripping composition of the present invention, photoresists can be removed at temperatures as low as 70° C. or lower. After removing photoresists, the treated substrate may be rinsed with an organic solvent such as alcohols or water.

The substrate to be treated by the method of the present invention may contain semiconductor wiring materials such as silicon, amorphous silicon, polysilicon, silicon oxide layer, silicon nitride layer, copper, copper alloy, aluminum, aluminum alloy, gold, platinum, silver, titanium, titanium-tungsten, titanium nitride, tungsten, tantalum, tantalum compound, chromium, chromium oxide, chromium alloy, and indium-tin-oxide (ITO); compound semiconductors such as gallium-arsenic, gallium-phosphorus and indium-phosphorus; dielectric materials such as strontium-bismuth-tantalum; and LCD substrate materials such as glass.

The present invention will be described in more detail with reference to the following examples which should not be construed to limit the scope of the present invention thereto.

EXAMPLES 1–9 AND COMPARATIVE
EXAMPLES 1–2

PFR-790 resist was applied to a substrate with tantalum/glass structure, and then, the resist was developed. Then, circuits were formed by dry etching using a fluorine compound. The resultant substrate was tested on the resist removal.

The substrate was immersed in a photoresist stripping composition at 40° C. After predetermined period of time, the substrate was taken out, rinsed with water, dried by blowing nitrogen gas, and observed under an optical microscope to determine the time required for removing the resist. The results are shown in Table 1.

TABLE 1

| | Alkaline compound (wt %) | Oxymethylamine compound (wt %) | Water (wt %) | Others (wt %) | Resist removing time (sec) |
|---|---|---|---|---|---|
| Examples | | | | | |
| 1 | EA (40) | BDE (0.01) | 20 | DMAC (39.99) | 45 |
| 2 | — | BDE (30) | 5 | DMAC (65) | 60 |
| 3 | EDA (40) | BDE (0.1) | 20 | DMAC (39.9) | 45 |
| 4 | EA (40) | DBM (0.1) | 15 | DGME (44.9) | 60 |
| 5 | BA (35) | BDM (1) | 9 | DGBE (55) | 30 |
| 6 | MEA (50) | DBM (0.1) | — | NMP (49.9) | 45 |
| 7 | EA (35) | BDE (0.1) | 15 | DMAC (44.9) Sorbitol (5) | 45 |
| 8 | PA (60) | BDE (0.1) | 20 | DMSO (19.9) | 30 |
| 9 | EA (80) | BDE (0.1) | — | PG (19.9) | 30 |
| Comparative Examples | | | | | |
| 1 | EA (40) | — | 20 | DMAC (40) | 150 |
| 2 | MEA (50) | — | — | NMP (50) | 600 |

Alkaline Compounds
EA: Ethanolamine
EDA: Ethylenediamine
BA: Butylamine
MEA: Methylethanolamine
PA: 1-amino-2-propanol
Oxymethylamine Compounds
BDE: (Butoxymethyl)diethylamine
DBM: Di(butoxymethyl)aminomethane
BDM: (Isobutoxymethyl)dimethylamine
Others
DMAC: Dimethylacetamide
DGME: Diethylene glycol monomethyl ether
DGBE: Diethylene glycol monobutyl ether
NMP: N-Methylpyrrolidone
DMSO: Dimethyl sulfoxide
PG: Propylene glycol

EXAMPLE 10

On an oxide layer, a barrier metal layer, an Al alloy (Al—Cu) layer and a barrier metal layer were laminated in this order to prepare a substrate for semiconductor device. By dry etching using a resist layer as the mask, Al-alloy wiring was formed, followed by ashing treatment using oxygen plasma. Ear-shaped resists remained on the side wall of the wiring, and streak resists remained on the wiring.

The resultant substrate was brought into contact, at 70° C. for 15 min, with a photoresist stripping composition consisting of 50% by weight of ethanolamine, 5% by weight of 4-t-butylcatechol, 0.5% by weight of (butoxymethyl)diethylamine, 19.5% by weight of diethylene glycol monobutyl ether, and 25% by weight of water. After rinsed with isopropanol and then super pure water, the substrate was dried and observed under a scanning electron microscope (SEM). The results showed that the resist residues were completely removed and no corrosion was found on the wiring.

EXAMPLES 11–17 AND COMPARATIVE EXAMPLES 3–4

A substrate for semiconductor device similar to one used in Example 10 was immersed in each photoresist stripping composition having the chemical composition shown in Table 2 at room temperature for a predetermined period of time. The substrate was then rinsed with super pure water, dried and observed under a scanning electron microscope (SEM) to evaluate the resist removal and the corrosion of wiring according to the following ratings.

Resist Removal
  A: Completely removed.
  B: Slightly remained.
  C: Not removed.

Corrosion of Wiring
  A: No corrosion.
  B: Slight roughness on wiring surface
  C: Corroded.

TABLE 2

| | Chemical Composition (% by weight) | | | |
|---|---|---|---|---|
| | Alkaline compound | Oxymethylamine compound | Water | Others |
| Examples | | | | |
| 11 | EA (50) | BDE (0.2) | 17 | NMP (29.8) CA (3) |
| 12 | DETA (30) | BDE (0.5) | 20 | DMSO (44.5) CA (5) |
| 13 | MEA (65) | DBM (0.9) | 10 | DGBE (24) BT (0.1) |
| 14 | PA (65) | BDE (1) | 18 | DGME (14) BuCA (2) |
| 15 | EA (30) TMAH (0.5) | BDE (0.5) | 8 | DMSO (56) Sorbitol (5) |
| 16 | EA (30) | EEA (2) | 26 | DPME (40) KA (2) |
| 17 | AEE (62.5) | DBM (0.5) | 30 | Xylitol (5) KA (2) |
| Comparative Examples | | | | |
| 3 | EA (50) | — | 17 | NMP (30) CA (3) |
| 4 | HA (30) | — | 30 | NMP (37) CA (3) |

Alkaline Compounds
EA: Ethanolamine
DETA: Diethylenetriamine
MEA: Methylethanolamine
PA: 1-amino-2-propanol
TMAH: Tetramethylammonium hydroxide
AEE: Aminoethoxyethanol
HA: Hydroxylamine
Oxymethylamine Compounds
BDE: (Butoxymethyl)diethylamine
DBM: Di(butoxymethyl)aminomethane
EEA: Ethoxymethyldiethylamine
Others
NMP: N-Methylpyrrolidone
CA: Catechol
DMSO: Dimethyl sulfoxide
DGBE: Diethylene glycol monobutyl ether
BT: Benzotriazole
DGME: Diethylene glycol monomethyl ether
BuCA: 4-Tert-butylcatechol
KA: Citric acid

EXAMPLES 18–21 AND COMPARATIVE EXAMPLES 5–6

On a glass substrate, a SiO$_2$ layer, a low-temperature polysilicon (p-Si) layer with abut 400 Å thick and an insulating layer were formed in this order to prepare a substrate for thin film transistor. The low-temperature polysilicon layer was etched using a patterned photoresist layer as the mask. The test substrate after etching is cross-sectionally illustrated in FIG. 1. The insulating layer was partly etched away to expose the underlying low-temperature silicon layer to a photoresist stripping composition.

The test substrate was immersed in a photoresist stripping composition at 40° C. After predetermined period of time, the substrate was taken out, rinsed with water, dried by blowing nitrogen gas, and observed under an optical microscope to determine the time required for removing the resist. Simultaneously, the corrosion was observed and evaluated by the following ratings.

A: No corrosion.
B: Slightly corroded.
C: Polysilicon layer was lost by corrosion.

The results are shogun in Table 3.

TABLE 3

| | Alkaline compound (wt %) | Oxymethylamine compound (wt %) | Water (wt %) | Others (wt %) | Resist removing time (sec) | Corrosion |
|---|---|---|---|---|---|---|
| Examples | | | | | | |
| 18 | EA (70) | BDE (0.05) | — | DMAC (29.95) | 30 | A |
| 19 | MEA (50) | BDE (0.1) | 5 | DMSO (44.9) | 60 | A |
| 20 | DMEA (40) | BDE (0.1) | 20 | DGME (39.9) | 90 | A |
| 21 | DEEA (30) HA (5) | BDE (0.1) | 24.9 | TGDM (40) | 30 | A |
| Comparative Examples | | | | | | |
| 5 | EA (70) | — | — | DMAC (30) | 90 | C |
| 6 | MEA (50) | — | — | DMSO (50) | 180 | B |

Alkaline Compounds
EA: Ethanolamine
MEA: Methylethanolamine
DMEA: N,N-Dimethylethanolamine
DEEA: Diethylaminoethanol
HA: Hydroxylamine
Oxymethylamine Compounds
BDE: (Butoxymethyl)diethylamine
Others
DMAC: Dimethylacetamide
DMSO: Dimethyl sulfoxide
DGME: Diethylene glycol monomethyl ether
TGDM: Triethylene glycol dimethyl ether

EXAMPLE 22

Synthesis of (2-methoxy-2-ethoxyethoxymethyl)diethylamine

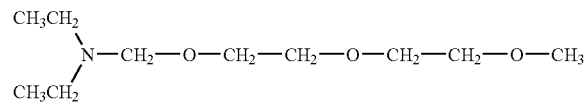

Into diethylamine (40.0 g, 0.548 mol), were added 30% formalin (73.1 g, 0.731 mol) and diethylene glycol monomethyl ether (87.7 g, 0.731 mol) under stirring in the presence of potassium carbonate (60 g).

Figure 2:
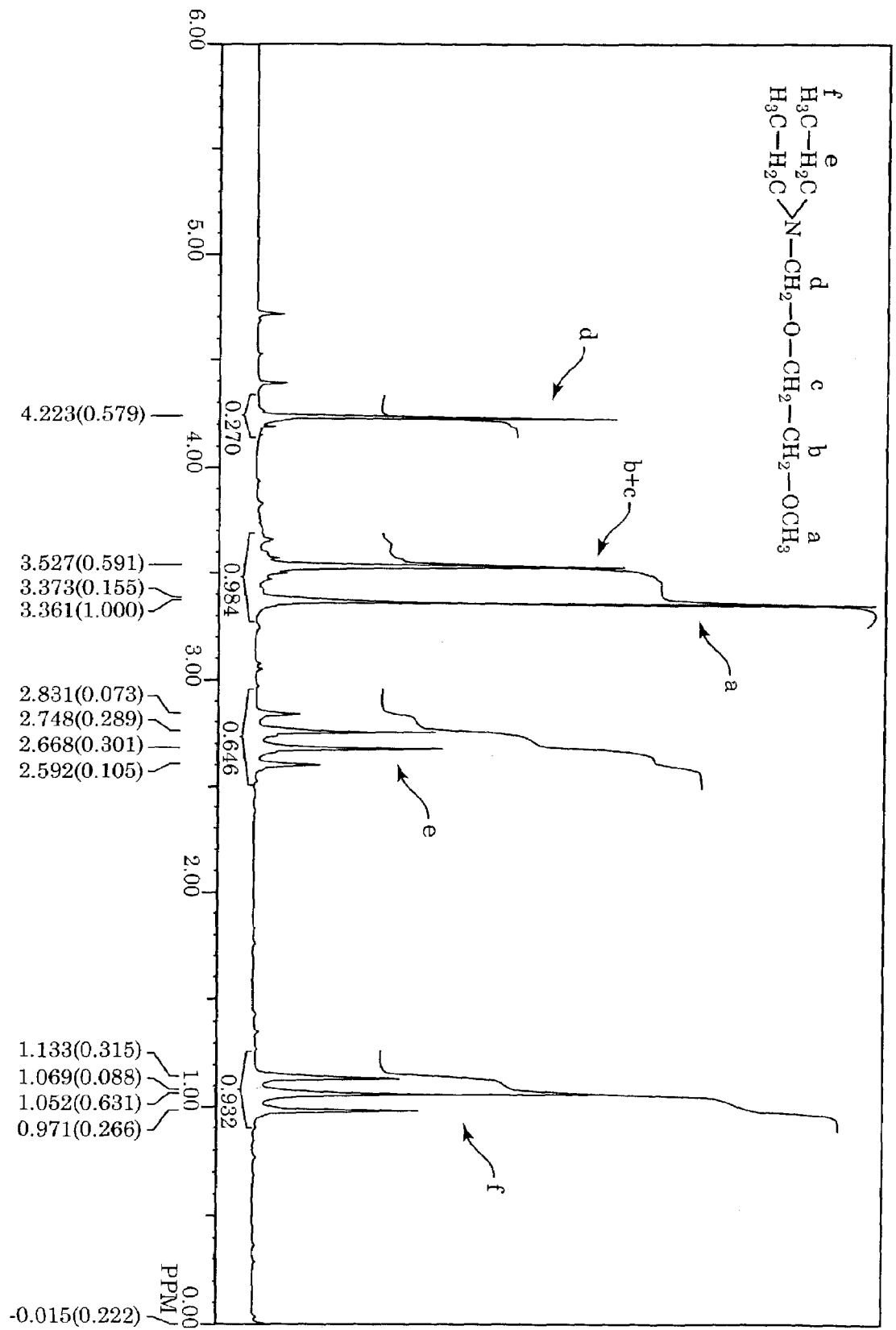
FIG. 2 is a $^1$H-NMR chart of (2-methoxy-2-ethoxyethoxymethyl)diethylamine prepared in Example 22.

After 19 hr, the oil component was extracted by a separatory funnel, dried over potassium carbonate (5 g), distilled at about 1 mmHg and 87° C. to obtain the titled compound as a colorless liquid. The yield was 56%. The chemical structure was identified by $^1$H-NMR (solvent: CDCl$_3$; concentration: 5%; reference: TMS; temperature; room temperature). The NMR chart is shown in FIG. 2.

The titled compound was a water-soluble liquid having a weak amine smell.

EXAMPLE 23

Synthesis of (2-methoxy-2-ethoxyethoxymethyl)dimethylamine

The reaction was repeated in the same manner as in Example 22 except for changing diethylamine to dimethylamine. After the reaction, the titled compound was obtained through hexane extraction, distillation and purification. The yield was 10%. The titled compound was a water-soluble liquid having a weak amine smell.

EXAMPLE 24

Synthesis of (2-methoxy-1-methylethoxymethyl)diethylamine

The reaction was repeated in the same manner as in Example 22 except for changing diethylene glycol monomethyl ether to methoxyisopropanol. After the reaction, the titled compound was obtained through hexane extraction, distillation and purification. The yield was 40%.

COMPARATIVE EXAMPLE 7

Synthesis of diethyl(butoxymethyl)amine

The synthesis was carried out according to the method described in G. M. Robinson, R. Robinson, J. Chem. Soc., 123, 523 (1923). The resultant amine was separated out from water and had a very strong amine smell.

EXAMPLES 25–29 AND COMPARATIVE EXAMPLES 8–10

In the same manner as in Examples 18–21 and Comparative Examples 5–6, the resist removal and the corrosion of polysilicon were evaluated. The results are shown in Table 4.

TABLE 4

| | Alkaline compound (wt %) | Oxymethylamine compound (wt %) | Water (wt %) | Others (wt %) | Resist removing time (sec) | Corrosion |
|---|---|---|---|---|---|---|
| Examples | | | | | | |
| 25 | EA (70) | MEEA (0.05) | — | DMSO (29.95) | 30 | A |
| 26 | MEA (10) | MEEA (0.1) | 5 | DMAC (84.9) | 60 | A |
| 27 | — | MEMA (40) | 20 | DGME (40) | 90 | A |
| 28 | DEEA (30) HA (5) | MEEA (0.1) | 24.9 | TGDM (40) | 30 | A |
| 29 | — | MEEA (100) | — | — | 30 | A |
| Comparative Examples | | | | | | |
| 8 | EA (70) | — | — | DMSO (30) | 90 | A |
| 9 | MEA (10) | — | — | DMAC (90) | 180 | C |
| 10 | DMEA (40) | — | 20 | DGME (40) | 360 | B |

Alkaline Compounds
EA: Ethanolamine
MEA: Methylethanolamine
DEEA: Diethylaminoethanol
HA: Hydroxylamine
DMEA: N,N-Dimethylethanolamine
Oxymethylamine Compounds
MEEA: (2-methoxy-2-ethoxyethoxymethyl)diethylamine
MEMA: (2-methoxy-2-ethoxyethoxymethyl)dimethylamine
Others
DMSO: Dimethyl sulfoxide
DMAC: Dimethylacetamide
DGME: Diethylene glycol monomethyl ether
TGDM: Triethylene glycol dimethyl ether By using the photoresist stripping composition of the present invention, photoresists can be easily removed without corrosion of wiring materials, etc. in a short period of time. Particularly, the oxymethylamine compound of formula 1 wherein $R^1$ is the ether linkage-containing substituent is less smelling and water-soluble, and can be produced from inexpensive starting materials. A cleaning composition or a photoresist stripping composition containing such an oxymethylamine compound removes photoresists without corrosion of wiring materials, etc. in a short period of time.

What is claimed is:

1. A photoresist stripping composition containing at least one oxymethylamine compound having an alkoxymethylamine structure or an alkoxymethylamine structure substituted by an ether linkage-containing substituent, wherein the oxymethylamine compound is represented by the following formula 1:

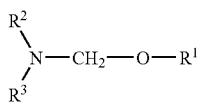

(1)

wherein $R^1$ is alkyl group, hydroxyalkyl group, aryl group, acyl group, alkoxyalkyl group, aminoalkyl group, or ether linkage-containing substituent; $R^2$ is alkyl group, acyl group, hydroxyalkyl group, aryl group, allyl group, aminoalkyl group, alkoxyalkyl group, hydroxyl group, or amino group; $R^3$ is alkyl group, acyl group, hydroxyalkyl group, aryl group, allyl group, aminoalkyl group, alkoxyalkyl group, hydroxyl group, or amino group; provided that $R^2$ and $R^3$ together with the nitrogen to which $R^2$ and $R^3$ are bonded may form a ring structure when each of $R^2$ and $R^3$ is a group having 1 to 8 carbon atoms.

2. The photoresist stripping composition according to claim 1, wherein $R^1$ of formula 1 is alkyl group, hydroxyalkyl group or alkoxyalkyl group.

3. The photoresist stripping composition according to claim 1, wherein the oxymethylamine compound having the alkoxymethylamine structure substituted by the ether linkage-containing substituent is represented by the following formula 7:

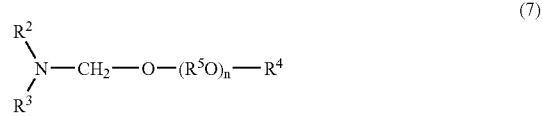

(7)

wherein $R^2$ and $R^3$ are as defined above; $R^4$ is alkyl group having 1 to 8 carbon atoms; $R^5$ is alkylene group having 1 to 4 carbon atoms; and n is an integer from 1 to 4; provided that two to four $R^5$ groups when n is an integer from 2 to 4 are either the same or different.

4. The photoresist stripping composition according to claim 3, wherein the oxymethylamine compound is represented by the following formula 8:

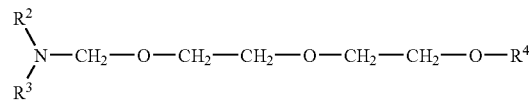

(8)

wherein $R^2$, $R^3$ and $R^4$ are as defined above.

5. The photoresist stripping composition according to claim 3, wherein the oxymethylamine compound is represented by the following formula 9:

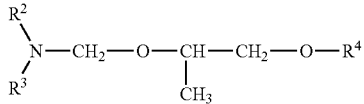

(9)

wherein $R^2$, $R^3$ and $R^4$ are as defined above.

6. The photoresist stripping composition according to claim 1, further containing an alkaline compound.

7. The photoresist stripping composition according to claim 6, wherein the alkaline compound is at least one compound selected from the group consisting of alkylamines, alkanolamines, polyamines, hydroxylamines, cyclic amines and quaternary ammonium hydroxides.

8. The photoresist stripping composition according to claim 1, further containing an anti-corrosion agent.

9. The photoresist stripping composition according to claim 8, wherein the anti-corrosion agent is at least one compound selected from the group consisting of aromatic hydroxy compounds, sugar alcohols, triazole compounds, and chelating compounds.

10. The photoresist stripping composition according to claim 1, further containing water.

11. The photoresist stripping composition according to claim 6, comprising 0.001 to 99.999% by weight of the oxymethylamine compound and 0.001 to 99.999% by weight of the alkaline compound.

12. A method for removing photoresist comprising a step of removing photoresists remaining after formation of wiring on a substrate for semiconductor devices or liquid crystal display devices by contacting the substrate with the photoresist stripping composition according to claim 1.

13. An oxymethylamine compound represented by the following formula 7:

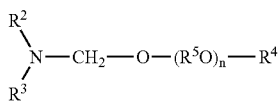

(7)

wherein $R^2$ is hydrogen, alkyl group, acyl group, hydroxyalkyl group, aryl group, allyl group, aminoalkyl group, alkoxyalkyl group, hydroxyl group, or amino group; $R^3$ is hydrogen, alkyl group, acyl group, hydroxyalkyl group, aryl group, allyl group, aminoalkyl group, alkoxyalkyl group, hydroxyl group, or amino group, provided that $R^2$ and $R^3$ together with the nitrogen to which $R^2$ and $R^3$ are bonded may form a ring structure when each of $R^2$ and $R^3$ is a group having 1 to 8 carbon atoms; $R^4$ is alkyl group having 1 to 8 carbon atoms; $R^5$ is alkylene group having 1 to 4 carbon atoms; and n is an integer from 1 to 4, provided that two to four $R^5$ groups when n is an integer from 2 to 4 are either the same or different.

14. The oxymethylamine compound according to claim 13, represented by the following formula 8:

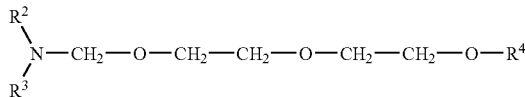

(8)

wherein $R^2$, $R^3$ and $R^4$ are as defined above.

15. The oxymethylamine compound according to claim 13, represented by the following formula 9:

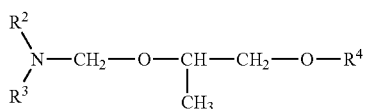

(9)

wherein $R^2$, $R^3$ and $R^4$ are as defined above.

16. The oxymethylamine compound according to claim 13, represented by the following formula 4:

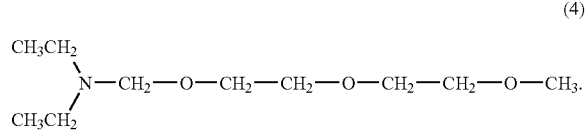

(4)

17. The oxymethylamine compound according to claim 13, represented by the following formula 5:

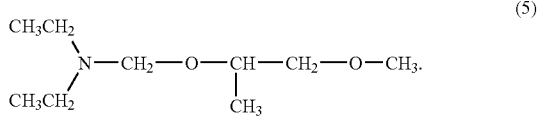

(5)

18. A cleaning composition for semiconductor devices, containing at least one oxymethylamine compound as defined in claim 13.

19. A photoresist stripping composition containing at least one oxymethylamine compound as defined in claim 13.

20. The photoresist stripping composition according to claim 7, further containing an organic solvent.

21. The photoresist stripping composition according to claim 6, further containing an organic solvent.

22. The photoresist stripping composition according to claim 5, further containing an organic solvent.

23. The photoresist stripping composition according to claim 4, further containing an organic solvent.

24. The photoresist stripping composition according to claim 3, further containing an organic solvent.

25. The photoresist stripping composition according to claim 2, further containing an organic solvent.

26. The photoresist stripping composition according to claim 8, further containing an organic solvent.

27. The photoresist stripping composition according to claim 1, further containing an organic solvent.

28. A photoresist stripping composition containing at least one oxymethylamine compound selected from the group consisting of (butoxymethyl)diethylamine, (methoxymethyl)diethylamine, (methoxymethyl)dimethylamine, (butoxymethyl)dimethylamine, (isobutoxymethyl)dimethylamine, N-(methoxymethyl)morpholine, N-(butoxymethyl)morpholine, N-(methoxymethyl)piperidine, N-(butoxymethyl)piperidine, di(methoxymethyl)aminoethane, di(methoxymethyl)aminomethane, di(butoxymethyl)aminoethane, di(butoxymethyl)aminomethane, di(methoxymethyl)aminoethanol, di(butoxymethyl)aminoethanol, di(methoxymethyl)aminoethoxyethanol, di(butoxymethyl)aminoethoxyethanol, di(methoxymethyl)aminoethoxymethane, methyl(methoxymethyl)aminoethane, methyl(methoxymethyl)aminoethanol, methyl(butoxymethyl)aminoethanol, di(methoxymethyl)aminopropanol, di(butoxymethyl)aminopropanol, di(methoxymethyl)aminoisopropanol, di(butoxymethyl)aminoisopropanol, N,N-di(methoxymethyl)-N',N'-dimethylethylenediamine, N,N'-di(methoxymethyl)piperazine, di(butoxymethyl)piperazine, (methoxymethyl)diethanolamine, (hydroxyethyloxymethyl)diethylamine and oxymethylamine compounds represented by the following formula 7:

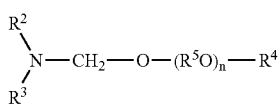

(7)

wherein $R^2$ is hydrogen, alkyl group, acyl group, hydroxyalkyl group, aryl group, allyl group, aminoalkyl group, alkoxyalkyl group, hydroxyl group or amino group; $R^3$ is hydrogen, alkyl group, acyl group, hydroxyalkyl group, aryl group, allyl group, aminoalkyl group, alkoxyalkyl group, hydroxyl group or amino group, provided that $R^2$ and $R^3$ together with the nitrogen to which $R^2$ and $R^3$ is a group having 1 to 8 carbon atoms; $R^4$ is alkyl group having 1 to 8 carbon atoms; $R^5$ is alkylene group having 1 to 4 carbon atoms; and n is an integer from 1 to 4, provided that two to four $R^5$ groups when n is an integer from 2 to 4 are either the same or different.

29. The photoresist stripping composition according to claim 28, further containing an alkaline compound.

30. The photoresist stripping composition according to claim 29, wherein the alkaline compound is at least one compound selected from the group consisting of alkylamines, alkanolamines, polyamines, hydroxylamines, cyclic amines and quaternary ammonium hydroxides.

31. The photoresist stripping composition according to claim 28, further containing an organic solvent.

32. The photoresist stripping composition according to claim 28, further containing an anti-corrosion agent.

33. The photoresist stripping composition according to claim 28, further containing water.

34. The photoresist stripping composition according to claim 28, comprising 0.001 to 99.999% by weight of the oxymethylamine compound and 0.001 to 99.999% by weight of the alkaline compound.

35. A method for removing photoresist comprising a step of removing photoresist remaining after formation of wiring on a substrate for semiconductor devices or liquid crystal display devices by contacting the substrate with the photoresist stripping composition according to claim 28.

* * * * *